United States Patent [19]

Hotten

[11] 3,954,918

[45] May 4, 1976

[54] BISPHOSPHORAMIDES AND PROCESS FOR PREPARING THE SAME

[75] Inventor: Bruce W. Hotten, Orinda, Calif.

[73] Assignee: Chevron Research Company, San Francisco, Calif.

[22] Filed: Sept. 5, 1974

[21] Appl. No.: 499,675

Related U.S. Application Data

[62] Division of Ser. No. 284,012, Aug. 25, 1972, Pat. No. 3,868,376.

[52] U.S. Cl. .............................. 260/929; 260/928; 260/974; 260/984
[51] Int. Cl.$^2$ ............................................ C07F 9/24
[58] Field of Search ............ 260/928, 929, 974, 984

[56] References Cited

UNITED STATES PATENTS 2,974,158    3/1961    Lanham .................... 260/929 X Primary Examiner—Anton H. Sutto
Attorney, Agent, or Firm—G. F. Magdeburger; C. J. Tonkin

[57] ABSTRACT

Novel bisphosphoramides are prepared by reacting phosphorus oxychloride with a hydrocarbyl diol difunctional compound and a dihydrocarbyl amine monofunctional compound.

5 Claims, No Drawings

BISPHOSPHORAMIDES AND PROCESS FOR PREPARING THE SAME

This is a division of application Ser. No. 284,012, filed Aug. 25, 1972, now U.S. Pat. No. 3,868,376.

BACKGROUND OF THE INVENTION

This invention relates to novel phosphorus containing compounds and to a method of preparing the same. More particularly, the invention relates to bisphosphoramides having superior anti-wear properties.

The employment of anti-wear agents in motor oils, fuels, transmission fluids, hydraulic fluids, etc., is well established. Numerous types of additives have been developed and several have proved quite successful in reducing wear and increasing equipment life. Typical anti-wear agents which have experienced commercial success include zinc dihydrocarbyl dithiophosphates, zinc dialkyldithiocarbamate, tricresyl phosphate, dilauryl phosphate, di-dodecyl phosphite, sulfurized turpenes, sulfurized sperm oil, various chlorinated compounds, etc. Of the above compounds zinc dihydrocarbyl dithiophosphate and tricresyl phosphate have essentially dominated the field.

While the conventional anti-wear agents have performed satisfactorily in the older equipment, the introduction of more powerful and higher speed machines has encouraged the development of anti-wear agents having superior anti-wear properties not heretofor obtainable. In addition, several ancillary problems appurtenant with many of the conventional anti-wear agents have encouraged the search for an improved additive. For example, the employment of zinc dihydrocarbyl dithiophosphate or other metal containing anti-wear agents is burdened with a relatively high ash content. Another problem is the diminution of raw materials employed to produce some of the additives, e.g., the reduction of the availability of sperm oil, etc.

In addition to the anti-wear properties, in many instances it is advantageous to modify the friction properties of a lubricant. The conventional anti-wear agents do not exhibit these friction modifying properties and, accordingly other additives must be employed to obtain this effect thereby increasing the cost and ash content of the final composition. Thus a need exists for an additive having improved anti-wear properties, that does not have a high ash content, that is relatively inexpensive to make and that exhibits friction modifying properties.

It is therefore an object of this invention to provide an improved anti-wear agent.

It is another object of this invention to provide an ashless anti-wear agent.

Another object of this invention is to provide an anti-wear agent having friction modifying properties.

Another object of this invention is to provide an anti-wear gent having superior anti-wear properties, which exhibits friction modifying properties, and which has a low ash content.

Another object of this invention is to provide a method for preparing an improved anti-wear agent.

Other objects of this invention will become apparent from the following description of the invention and appended claims.

SUMMARY OF THE INVENTION

The aforementioned objects and their attendant advantages can be realized with a bisphosphoramide compound having the structure:

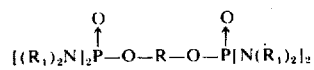

wherein:

R is a hydrocarbylene having from 2 to 18 carbons and preferably from 2 to 8 carbons; and $R_1$ is the same or different hydrocarbyl having from 1 to 24 carbons and preferably from 6 to 20 carbons.

As referred to herein, hydrocarbyl is a monovalent organic radical composed essentially of hydrogen and carbon and may be aliphtic, aromatic, or alicyclic or combinations thereof; e.g., aralkyl, alkyl, aryl, cycloalkyl, alkylcycloalkyl, etc., and may be saturated or ethylenically unsaturated (one or more double bonded carbons, conjugated or nonconjugated). The preferred hydrocarbyl is an alkyl. The hydrocarbylene, as defined herein, is a divalent hydrocarbon radical which may be aliphatic, alicyclic, aromatic or combinations thereof; e.g., alkylene, arylene, alkylarylene, aralkylene, alkylcycloalkylene, cycloalkylarylene, etc., having its two free valences on different carbon atoms. The preferred hydrocarbylene is an alkylene.

We have found that the bisphosphoramides having the structure shown above exhibit superior anti-wear characteristics and in some instances have anti-wear properties which are not heretofore obtainable with conventional additives. While the exact mechanism involved in sharply ameliorating wear is unknown, it is believed that the bisphosphoramide coats the exposed metallic parts with a thin, perhaps monomolecular, layer of the protective compound which strongly adheres to the metal surface. The hydrocarbon component extends from the center phosphorus atoms and, it is believed, retards the loss off lubricant from the boundary layer and, also, provides some protection against direct abrasion. This mechanism is only a hypothesis and should not be held as binding on the claimed invention, since in any event it is shown with working examples that the bisphosphoramides substantially reduce wear.

Exemplary bisphosphoramides which may be employed in the practice of this invention include diethylene glycol bis(tetracocophosphoramide.

DETAILED DESCRIPTION OF THE INVENTION

The bisphosphoramides of this invention are prepared by reacting phosphorus oxychloride with a difunctional secondary alcohol and a monofunctional amine. The reaction can be conducted non-catalytically by merely contacting the three reactants within a suitable reaction vessel at a temperature from 0° to 200°C and preferably from 20° to 150°C. The reaction pressure is not critical except that it is preferred to apply sufficient pressure on the system to maintain liquid phase conditions. Generally, the pressure will range from 10 to 500 psia and preferably from 14 to 35 psia. The reaction time varies depending upon the type of reactants selected, reaction conditions selected, etc., however, it generally varies from 10 minutes to 10 hours and preferably from 30 minutes to 3 hours.

The difunctional alcohol forms the bridging group between the two phosphorus atoms as shown in the structural formula supra. The monofunctional amine, on the other hand, reacts with remaining halogens on the phosphorus oxychloride molecules to form the four terminal groups extending from the phosphorus atoms.

The difunctional compounds which may be employed in the practice of this invention include $C_2$ to $C_{24}$ primary diols such as trimethylene glycol, ethylene glycol, diethylene glycol, triethylene glycol, propentylene glycol, dipropylene glycol, tetra-methylene glycol, n-propane-1,3-diol, 2-butene-1,4-diol, 2,2'-thiodiethanol, neopentyl glycol, hydroquinone, chlorohydroquinone, naphthoquinone, phenyl-1,2-ethanediol, 2-anilino-1,4-naphthohydroquinone, 2,7-dihydroxynaphthalene, etc. The preferred difunctional hydroxy reactants have from 2 to 12 carbons.

The mono functional compounds which may be employed in the practice of this invention have the following general formula:

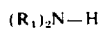

wherein $R_1$ is defined supra under the description of the bisphosphoramide general formula. Exemplary monoamines include primary alkyl amines such as heptylamine, octylamine, dodecylamine, tetradecylamine, hexadecylamine, octadecylamine, etc; secondary alkyl amines such as, diheptylamine, N,N-ethylhexylamine, N,N-hexyloctylamine, dioctylamine, and N,N-butylhexylamine, etc.; primary and secondary cycloalkyl and alkylcycloalkyl amines such as 2-ethylcyclohexylamine, N,N-ethylcyclohexylamine, N,N-methylcyclohexylamine, N,N-propylcyclohexylamine, dicyclohexylamine, N,N-ethylcyclopentylamine, 2-propyl-3-ethylcyclohexylamine, etc; and primary and secondary aryl and alkylarylamines such as methylaniline, toluidine, N,N-ethylphenylamine, p-anisidine, nitroaniline, diphenylamine, N,N-propylphenylamine, 2,4,6 trichloroaniline, N,N-octylphenylamine, p-phenetidine, etc.

Particularly preferred monoamines are prepared from vegetable oils and fats. Typical natural oils and fats which may be employed in preparing the monofunctional compounds include coconut oil, corn oil, rape oil, castor oil, peanut oil, cottonseed oil, linseed oil, olive oil, palm oil, safflower oil, soybean oil, sperm oil, tung oil, etc. These oils are generally comprised of a mixture of saturated and unsaturated fatty acids such as caprylic, capric, lauric, myristic, palmitic, stearic, arachidic, palmitoleic, oleic, ricinoleic, linoleic, eleostearic, etc. The fatty acids are converted into the corresponding primary or secondary amine, alcohol or mercaptan by conventional processing means.

The preferred monofunctional compounds are the $C_{10}$–$C_{30}$ primary and secondary vegetable oil amines such as caprylamine, dicaprylamine, laurylamine, dilaurylamine, myristylamine, dimyristylamine, palmitylamine, dipalmitylamine, etc. and mixtures thereof.

The bisphosphoramides may be prepared by either a batch or continuous processing scheme. In a typical batch process, a reaction vessel, preferably constructed or lined with a corrosive resistant material such as glass, teflon, etc., is charged with a suitable inert reaction solvent and the difunctional and monofunctional compounds. The contents of the reactor are stirred to disperse the reactants within the reaction solvent. The phosphorus oxychloride is then introduced into the reaction vessel in contact with the other reactants. Preferably, the contacting is conducting at a temperature of about 20° to 150°C and at pressure sufficient to maintain a liquid phase reaction medium. The reaction takes place spontaneously upon the contacting of these reactants to produce the bisphosphoramide. Since the reaction is also exothermic, care must be taken in the introduction of the reactants in order to avoid rapid increases in localized temperatures. Preferably, the phosphorus reactant is introduced into the vessel at a rate of 5 to 25 mols per 50 mols of difunctional and monofunctional compounds per hour. This addition rate is not critical to the practice of this invention and only provides a convenient method of introducing the phosphorus reactant into the system without the problems of spontaneous boiling. For example, the phosphorus oxychloride may be charged to the reaction vessel before either the difunctional or monofunctional reactant, or in another alternative embodiment, the reactants may be charged to the vessel in an intermittent manner. The reaction can also be conducted adiabatically with the heat of reaction effecting the necessary temperature increase in the system.

When a dihydroxy difunctional reactant and amine monofunctional reactants are employed, it is, likewise, preferred to introduce the less restrictive dihydroxy reactant into contact with the phosphorus oxychloride prior to the addition of the amine reactant.

During the course of the reaction, hydrogen chloride is released as a by-product. This by-product can be stripped from the reaction medium during or after the completion of the reaction. While stripping may be a convenient method for removing the material, the conditions employed during the stripping steps in many instances have an adverse effect on the product bisphosphoramide. Therefore, it is preferred to complex or neutralize the hydrogen chloride within the reaction medium concomitant with its formation. I have found that the complexing or neutralization step can be accomplished by admixing a stable basic compound or acid acceptor within the reaction medium. These acid acceptors should also be inert to the reactants and bisphosphoramide product. Exemplary acid acceptors include $C_1$ to $C_{20}$ trialkyl amines such as trimethylamine, triethylamine, tripropylamine, triisopropylamine, tributylamine, etc., basic hetarenes, such as pyridine, quinoline, picoline, pyrazine, etc., as well as basic metal compounds such as magnesium oxide, calcium oxide, calcium carbonate, magnesium carbonate, alkaline earth metal hydroxides such as magnesium hydroxide, calcium hydroxide, barium hydroxide, etc., and alkali hydroxides such as sodium hydroxide, potassium hydroxide and lithium hydroxide.

The preferred acid acceptors are the trialkyl amines and hetarenes since water is not produced in the neutralization of the hydrogen chloride by-product. The presence of water in the system is to be avoided since it may react with the phosphorus oxychloride reactant.

The crude bisphosphoramide can then be filtered to remove the liquid reaction medium and unreacted reactants. Although filtering is preferred, it is recognized that alternative purification steps can be performed such as extraction, stripping, etc.

As discussed supra, the reaction is preferably conducted in the presence of an inert stable reaction solvent. Exemplary reaction solvents which may be employed in the practice of this invention include $C_5$ to C₂₀ aliphatic or aromatic hydrocarbons such as hexane, octane, nonane, benzene, toluene, naphthalene, ethylcyclohexene, etc., halogenated hydrocarbons, hydrocarbon esters, hydrocarbon ethers, hydrocarbon amides, etc., may be employed.

The concentration of the various reactants within the reaction medium can vary over a wide range depending upon the reactants chosen, the reaction conditions, vessel construction, processing scheme, etc. Generally, however, the reactants will be present in the amounts shown in the following Table 1.

TABLE 1

| COMPONENT | BROAD RANGE (weight %) | PREFERRED RANGE (weight %) |
|---|---|---|
| Reaction Solvent | 40 – 80 | 60 – 70 |
| Difunctional Compound | 1 – 10 | 2 – 5 |
| Monofunctional Compound | 10 – 50 | 20 – 40 |
| Acid Acceptor | 5 – 30 | 10 – 20 |
| Phosphorus Oxychloride[1] | 4 – 15 | 6 – 10 |

[1]Based on the amount introduced into the reaction medium

The molar ratio of the reactants introduced into the reaction medium will generally vary from 3 to 5 mols of monofunctional compound and 0.4 to 0.6 mols of difunctional compound per mol of phosphorus compound. Preferably the reactants are present in substantially stoichiometric amounts.

The bisphosphoramides of this invention can be incorporated into a lubricating oil to realize a lubricant having superior anti-wear properties. The amount of bisphosphoramide which may be present within the lubricating oil to impart the desired anti-wear properties varies depending upon the type of bisphosphoramide employed, the type of lubricating oil used, the presence of other additives, etc. Generally, however, the amount of bisphosphoramide within the lubricating oil will vary from 0.01 to 10 weight per cent and usually from 0.05 to 2 weight per cent based on the weight of the final lubricant composition.

The lubricating oil which may be employed in the practice of this invention includes a wide variety of hydrocarbon oils. Other oils include lubricating oils derived from coal products and synthetic oils, e.g., alkylene polymers (such as, polypropylene, butylene, etc., and mixtures thereof) alkylene oxide-type polymers (e.g., alkylene oxide polymers prepared by polymerizing alkylene oxide such as propylene oxide, etc., in the presence of water or alcohol, e.g., ethyl alcohol), carboxylic acid esters (e.g., those which were prepared by esterifying carboxylic acids such as adipic acid, azelaic acid, suberic acid, sebacic acid, alkenylsuccinic acid, fumaric acid, maleic acid, etc., with the alcohol such as butyl alcohol, hexyl alcohol, 2-ethylhexyl alcohol, pentaerythritol, etc., liquid esters of phosphorus, such as trialkyl phosphate (tributyl phosphate), dialkylaryl phosphate, triaryl phosphate (tricresyl phosphate), etc., alkylbenzenes, polyphenols (e.g., bisphenols and terphenols), alkylbiphenylethers, esters and polymers of silicon, e.g., tetraethyl silicate, tetraisopropyl silicate, hexyl(4-methyl-2-pentoxy) disilicate, poly(methyl)siloxane and poly(methylphenyl)siloxane, etc. The lubricating oils may be used individually or in combinations whenever miscible or whenever made so by use of mutual solvents. The lubricating oils generally have a viscosity which ranges from 50 to 5,000 SUS (Saybolt Universal Seconds) and usually from 100 to 1,500 SUS at 100°F.

In addition to the bisphosphoramide anti-wear agent, other additives may be successfully employed within the lubricating composition without affecting the superior anti-wear properties imparted by the bisphosphoramide. One type of additive is an anti-oxidant or oxidation inhibitor. This type of additive is employed to prevent varnish and sludge formation on metal parts and to inhibit corrosion of alloyed bearings. Typical anti-oxidants are organic compounds containing sulfur, phosphorus or nitrogen, such as organic amines, sulfides, hydroxysulfides, methanols, etc., alone or in combination with metals like zinc, tin or barium. Particularly useful anti-oxidants include phenyl-α-naphthylamine, bis(alkylphenyl)amine N,N'-diphenyl-p-phenylenediamine, 2,2,4-trimethyldihydroquinoline oligomer, bis(4-isopropylaminophenyl) ether, N-acylaminophenol, N-acylphenothiazines, N-hydrocarbylamides or ethylenediamine tetraacetic acid, alkylphenol-formaldehydeamine polycondensates, etc.

Another additive which may be employed is a rust inhibitor. The rust inhibitor is employed in all types of lubricants to suppress the formation of rust on the surface of metallic parts. Exemplary rust inhibitors include sodium nitrite, alkenyl succinic acids and derivatives thereof, alkylthio-acetic acid and derivatives thereof, substituted imidazoles, amine phosphates, etc.

Another additive which may be incorporated into the lubricant composition is an anti-corrodant. The anti-corrodant is employed to inhibit oxidation so that the formation of acidic bodies is suppressed and to form films over the metal surfaces which decrease the effect of corrosive materials on exposed metallic parts. Typical anti-corrodants are organic compounds containing active sulfur, phosphorus or nitrogen, such as organic sulfides, phosphides, metal salts of thiophosphoric acid, cyclic and acyclic epoxides and sulfurized waxes, barium phenates and sulfonates, etc. A particularly effective corrosion inhibitor is ammonium dinonylnaphthalenesulfonate.

Other types of lubricating oil additives which may be employed in combination with the bisphosphoramides of this invention include anti-foam agents (e.g., silicones, organic copolymers), stabilizers, anti-stain agents, tackiness agents, anti-chatter agents, dropping point improvers, anti-squawk agents, lubricating color correctors, extreme pressure agents, odor control agents, dispersants, detergents, etc. as well as other anti-wear agents such as tricresyl phosphate and zinc dithiophosphate esters.

The anti-wear agents of this invention can be employed in grease compositions to increase the bearing life and other endurance properties of the grease. These agents may successfully be employed with such thickening agents as polyurea compounds as disclosed in U.S. Pat. Nos. 3,232,210; 3,281,361; 3,346,497 and 3,401,027; calcium stearates, lithium stearates, aluminum complexes such as disclosed in U.S. Pat. Nos. 2,599,553; 3,345,291 and 3,514,400, etc. Generally when employed in grease formulation, the bisphosphoramides will be present in an amount of 0.05 to 5 weight percent and preferably from 0.1 to 1 weight percent of the final grease composition.

In many instances it may be advantageous to form concentrates of the bisphosphoramide within a carrier liquid. The employment of concentrates provides a convenient method of handling and transporting the bisphosphoramide compounds for their subsequent dilution and use. The concentration of the bisphosphoramides within the concentrates may vary from 10 to 100 weight per cent although it is preferred to maintain the concentration between about 20 and 80 weight percent.

LUBRICANT PERFORMANCE

The lubricants containing the bisphosphoramide compounds of this invention have very good anti-wear properties and in many instances surpass the anti-wear properties of ubiquitous tricresyl phosphate and zinc dihydrocarbyl dithiophosphate. Moreover, the bisphosphoramides do not contain a metal component and, accordingly, have a very low ash content. The low ash content is an important property for high temperature and high speed machine lubricants.

In addition to the above, the bisphosphoramide lubricants exhibit a surprising friction modifying effect. It was discovered that many of the bisphosphoramide compounds substantially changed the friction characteristics of metallic surfaces. For example, it was found that long chain aliphatic groups on the bisphosphoramide substantially reduce the coefficient of friction. This property of the additive improves the lubricity of a lubricant and accordingly reduces the power loss between sliding parts.

When short chain groups such as ethylene and cyclohexane are attached to the bisphosphoramide component, the coefficient of friction is substantially increased. This aspect of the bisphosphoramide compound is advantageous in ball and roller bearings in which slippage of the rolling elements in the races causes metal damage and in traction gears wherein special synthetic oils have been used to increase traction by elastohydrodynamic action. Also, this type of additive can be used in clutch and brake services where a good grip is necessary to transmit power efficiently, e.g., transmission oils, etc.

It is thus apparent from the above that the bisphosphoramide lubricants of this invention can be tailored to have the desired friction characteristics as well as good anti-wear properties.

It should be well recognized that the instant bisphosphoramides may be successfully employed in lubricant applications wherein metal wear is a problem. Thus, the bisphosphoramides may be employed in lubricating oil such as motor oils, turbine oils, gear oils, railroad diesel engine oils, transmission fluids, hydraulic oils, tractor and truck diesel engine oils, two cycle gasoline engine oil, cutting oils, drilling oils, lapping, grinding and honing oils, lubricating oils for pneumatic devices such as jackhammers, sinkers, stoppers, drifters and down hole drills.

The bisphosphoramides may also be useful in mist lubricants. In a mist lubricating system the lubricant is atomized in a mist generator and carried through conduits by an air stream. The lubricant droplets are coalesced and collected at the lubricating site. Such systems permit simultaneous lubrication of several remote lubrication points from a central lubricant reservoir.

The following examples are presented to illustrate the practice of specific embodiments of this invention and should not be interpreted as limitations upon the scope of the invention.

EXAMPLE 1

In this example, diethylene glycol bis(tetracocophosphoramide) is prepared. A 1-liter resin flask equipped with a stirrer, turned down condenser, thermometer, dropping funnel and a nitrogen gas intlet tube is charged with 64 grams of triethylamine, 10.6 grams of diethylene glycol, 600 milliliters of toluene and 151 grams of di(hydrogenated coco)amine (mol wt. — 377). The mixture is heated to about 50°C and stirred to dissolve its reactants within the toluene. Phosphorus oxychloride is then slowly introduced into the vessel, further addition is terminated and the flask is heated to a temperature of 100°–110°C under refluxing conditions for a period of about 7½ hours. The flask is washed with water to remove the chloride ions and thereafter stripped of toluene. The bisphosphoramide product is calculated to have the following structure.

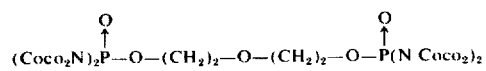

wherein Coco is the coconut oil fatty radical.

An analysis of the bisphosphoramide reveals the following:

|  | Calculated (weight %) | Found (weight %) |
| --- | --- | --- |
| Nitrogen | 3.3 | 3.16 |
| Phosphorus | 3.6 | 3.8 |

EXAMPLE 2

This example is presented to demonstrate the superior anti-wear properties of the bisphosphoramides of this invention over the monophosphoramides. In the test the first fluid is comprised solely of 480 neutral oil, and the second is 480 neutral oil containing 2 weight percent of diethyleneglycol bis(tetracocophosphoramide) prepared by the method of Example 1.

The fluids are tested in accordance with ASTM 2266-67 under the following test conditions

| Temperature | 130°F |
| Speed | 1800 rpm |
| Load | 20 kg. |
| Duration of Test | 1 hour |

The results of these tests are reported in the following Table 2.

TABLE 2

| ASTM FOUR-BALL WEAR TEST | |
| --- | --- |
| Test Compositions | Scar Diameter (mm) |
| 1. No additives | 0.76 |
| 2. Hexacocomonophosphoramide* | 0.75 |
| 3. Diethyleneglycol bis(tetracocophosphoramide) | 0.26 |

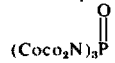

Coco represents the hydrocarbyl radical from coconut oil fatty amine and usually has an average of 12 carbons.

The above Table illustrates a sharp reduction in wear with a representative bisphosphoramide of this invention over either the base oil alone or with a monophosphoramide.

It is apparent that many widely different embodiments may be made without departing from the scope and spirit thereof; and, therefore, it is not intended to be limited except as indicated in the following ap-

I claim:
1. A composition of matter having the formula:

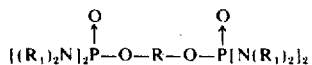

wherein:
R₁ is same or different hydrocarbyl from 1 to 24 carbon atoms; and
R is a hydrocarbylene having 2 to 18 carbon atoms.
2. The composition defined in claim 1 wherein said R₁ is an alkyl having from 6 to 20 carbon atoms.
3. The composition defined in claim 1 wherein said R₁ is a fatty radical obtained from coconut oil.
4. Diethylene glycol bis(tetracocophosphoramide).
5. A method for preparing novel bis-phosphoramides which comprises contacting within a liquid phase reaction medium (1) phosphorus oxychloride (2) a hydrocarbyl diol difunctional compound having 2 to 24 carbon atoms and (3) a dihydrocarbyl amine mono-functional compound having 1 to 24 carbon atoms, said contacting being conducted at a temperature of about 20° to 150°C and at a pressure sufficent to maintain a liquid phase reaction medium.

* * * * *